US012611170B2

(12) United States Patent
Oguri et al.

(10) Patent No.: US 12,611,170 B2
(45) Date of Patent: Apr. 28, 2026

(54) ULTRASOUND DIAGNOSTIC DEVICE CAPABLE OF CHANGING THE SOUND SPEED IN A LOCAL REGION

(71) Applicant: GE Precision Healthcare LLC, Waukesha, WI (US)

(72) Inventors: Takuma Oguri, Hino (JP); Naohisa Kamiyama, Hino (JP); Ryota Torii, Hino (JP)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/763,682

(22) Filed: Jul. 3, 2024

(65) Prior Publication Data

US 2025/0009335 A1     Jan. 9, 2025

(30) Foreign Application Priority Data

Jul. 7, 2023     (JP) ................................. 2023-112560

(51) Int. Cl.
　　*A61B 8/14*　　　(2006.01)
　　*A61B 8/00*　　　(2006.01)

(52) U.S. Cl.
　　CPC .............. *A61B 8/14* (2013.01); *A61B 8/4272* (2013.01); *A61B 8/463* (2013.01); *A61B 8/465* (2013.01); *A61B 8/469* (2013.01); *A61B 8/5207* (2013.01)

(58) Field of Classification Search
　　CPC ........ A61B 8/461; A61B 8/467; A61B 8/5269
　　See application file for complete search history.

(56) References Cited

U.S. PATENT DOCUMENTS

| | | | | |
|---|---|---|---|---|
| 2004/0210137 A1* | 10/2004 | Baba | ........................ | G06T 7/32 |
| | | | | 600/443 |
| 2008/0242999 A1* | 10/2008 | Kakee | ................. | G01S 7/52046 |
| | | | | 600/458 |
| 2011/0077521 A1* | 3/2011 | Katsuyama | .......... | A61B 8/4483 |
| | | | | 600/443 |

(Continued)

FOREIGN PATENT DOCUMENTS

| | | |
|---|---|---|
| JP | H06304172 A | 11/1994 |
| JP | H08308832 A | 11/1996 |

(Continued)

OTHER PUBLICATIONS

JP application 2023-112560 filed Jul. 7, 2023—Office Action issued Apr. 2, 2025; Machine Translation; 3 pages.

(Continued)

*Primary Examiner* — Nyrobi Celestine
(74) *Attorney, Agent, or Firm* — SPQ IP LLC

(57) ABSTRACT

An ultrasound diagnostic device generates an ultrasound image based on an echo signal from a subject. The ultrasound diagnostic device includes an ultrasonic probe that receives echo signals, an interface that allows an operator to designate position information of a local region of an ultrasound image, and signal processing means that changes the sound speed in the local region based on the position information when reconstructing the echo signals and reconstructing an ultrasound image, so that the sound speed is different from the sound speed in regions other than the local region. Herein, the local region is local in both the azimuth direction and the depth direction.

20 Claims, 4 Drawing Sheets

(56) References Cited

U.S. PATENT DOCUMENTS

| | | | | |
|---|---|---|---|---|
| 2014/0046606 A1* | 2/2014 | Torp | G01S 7/52074 | |
| | | | | 702/54 |
| 2014/0206999 A1* | 7/2014 | Ohta | A61B 8/467 | |
| | | | | 600/447 |
| 2015/0201909 A1* | 7/2015 | Yamamoto | A61B 8/585 | |
| | | | | 600/442 |
| 2015/0342568 A1* | 12/2015 | Kato | G01S 7/52049 | |
| | | | | 600/443 |
| 2020/0069971 A1* | 3/2020 | Sasaki | A61B 6/5229 | |
| 2023/0061869 A1* | 3/2023 | Rigby | G01S 7/52095 | |
| 2024/0057976 A1* | 2/2024 | McLaughlin | A61B 8/5269 | |

FOREIGN PATENT DOCUMENTS

| | | | |
|---|---|---|---|
| JP | 3710844 B2 * | 10/2005 | |
| JP | 2007007045 A | 1/2007 | |
| JP | 4817728 B2 * | 11/2011 | |
| JP | 2014140410 A | 8/2014 | |

OTHER PUBLICATIONS

JP2007007045 English Abstract; Espacenet.com Jul. 1, 2025; 1 page.
JP2014140410 English Abstract; Espacenet.com Jul. 1, 2025; 1 page.
JPH06304172 English Abstract; Espacenet.com Jul. 1, 2025; 1 page.
JPH08308832 English Abstract; Espacenet.com Jul. 1, 2025; 1 page.

* cited by examiner

ULTRASOUND DIAGNOSTIC DEVICE CAPABLE OF CHANGING THE SOUND SPEED IN A LOCAL REGION

CROSS-REFERENCE TO RELATED APPLICATION

This application claim priority to Japanese Patent Application No. 2023-112560, which was file on Jul. 7, 2023 at the Japanese Patent Office. The entire contents of the above-listed application are incorporated by reference herein in their entirety.

TECHNICAL FIELD

The present disclosure relates to an ultrasound diagnostic device that adjusts the sound speed of a designated local region and displays a sound speed-adjusted ultrasound image. In particular, the ultrasound diagnostic device adjusts the sound speed in a designated local region to be different from the sound speed outside the designated local region, and displays a sound speed-adjusted ultrasound image.

BACKGROUND

An ultrasound diagnostic device transmits ultrasonic waves from an ultrasonic probe having a plurality of ultrasonic transducers toward biological tissue of a subject. Ultrasonic echo signals are received by the plurality of ultrasonic transducers of the ultrasonic probe, and an ultrasound image is created based on the received echo signals.

The echo signals received at each of the ultrasound transducers are input to a reception beamformer. The reception beamformer performs reception beamforming on the echo signals received at each of the ultrasonic transducers. Reception beamforming includes a phase align and sum process in which echo signals received at each of the ultrasonic transducers are delayed and summed.

The delay time during reception beamforming is set by assuming that the sound speed of ultrasonic waves in biological tissue is a predetermined value (for example, 1530 m/s). However, the sound speed of ultrasonic waves in biological tissue may differ for each subject or each part of the body. For example, the sound speed in muscle may be 1590 m/s, and in bone may be 3000 m/s. If the sound speed set for determining the delay time differs from the actual sound speed, there is a risk that the reception focus will be degraded. If the sound speed set for determining the delay time differs from the actual sound speed, the spatial resolution deteriorates, and a preferable contrast cannot be obtained.

An ultrasound diagnostic device can displays patterns according to different diagnostic sites of a subject and according to the layered tissue structures of the diagnostic sites, and allows an examiner to manually change the sound speed of an ultrasonic signal to be applied to each layered tissue structure.

However, layer-based sound speed variation may not always meet the needs of the examiner. For example, lesions such as tumors and blood vessels may have sound speeds that differ from the surrounding tissue, but lesions such as tumors and blood vessels do not necessarily appear as layered structures in ultrasound images. For this reason, even if the examiner manually changes the sound speed for each of the plurality of layers, if the examiner wants to observe a plurality of structures, displaying all of the structures with desirable image quality might not be possible.

Therefore, there is a demand for an ultrasound diagnostic device that allows an examiner to easily change the sound speed in a local region as desired in an intuitive and easy-to-understand manner.

SUMMARY OF THE INVENTION

The ultrasound diagnostic device according to an aspect generates an ultrasound image based on an echo signal from a subject, including: an ultrasonic probe for receiving the echo signal; an interface that allows an operator to designate position information of a local region of an ultrasound image; and signal processing means for changing a sound speed value in the local region based on the position information so as to be different from a sound speed value in a region other than the local region when reconstructing the echo signal to reconstruct an ultrasound image. Here, the local region is local in both the azimuth direction and the depth direction.

With the ultrasound diagnostic device according to an aspect, the change in the sound speed value is performed according to a manual instruction by an operator, and the manual instruction is performed in accordance with one or more of: a slide operation by an operator of a slide bar displayed on a display device of the ultrasound diagnostic device; and input of a numerical value into a dialogue box displayed on a display device of the ultrasound diagnostic device by an operator.

The ultrasound diagnostic device of an aspect further includes a designation history storage unit that mutually associates and stores a past position designation history of the position information of the local region and a past manual sound speed designation history of the sound speed information of the local region. In addition, the signal processing means is configured to perform one or more of the following: returning the sound speed information setting to a previous state for one or more local regions included in the past position designation history; saving the sound speed information setting for one or more local regions included in the past position designation history; and loading previously set sound speed information for one or more local regions included in the past position designation history.

With the ultrasound diagnostic device of an aspect, the change in the sound speed is performed by analyzing an echo signal and/or an ultrasound image corresponding to the local region.

With the ultrasound diagnostic device of an aspect, the signal processing means calculates the sound speed of the local region based on a phase difference between elements of a reception signal and each element of an ultrasonic probe corresponding to the local region.

The ultrasound diagnostic device of an aspect further includes an image generating unit that displays a plurality of image items that are candidates for the local region by superimposing on the ultrasound image; wherein the plurality of image items are arranged in an azimuth direction and a depth direction, and position information of a local region is designated in response to selecting one or more of the plurality of image items.

With the ultrasound diagnostic device of an aspect, the size and/or number of the plurality of image items can be changed automatically or manually.

With the ultrasound diagnostic device of an aspect, a display manner is changed in response to one or more of the plurality of image items being selected, so that the selected one or more of the plurality of image items are distinguishable from one or more of the plurality of image items that were not selected.

With the ultrasound diagnostic device of an aspect, the signal processing means is configured to: generate an ultrasound image of the local region by reconstructing the echo signals using delay or sound speed parameters corresponding to the sound speed of the local region; and generate an ultrasound image of a region other than the local region by reconstructing the echo signal using delay or sound speed parameters corresponding to the sound speed of the region other than the local region.

An aspect provides a program for generating an ultrasound image based on an echo signal from a subject. The program causes a processor to perform: a step of receiving the echo signal; a step of receiving position information of a local region of an ultrasound image based on a designation by an operator; and a step of changing a sound speed in the local region based on the position information so as to be different from a sound speed in a region other than the local region when reconstructing the echo signal to reconstruct an ultrasound image. Here, the local region is local in both the azimuth direction and the depth direction. An eleventh aspect provides a non-transitory storage medium storing the program provided in the tenth aspect.

Effect of the Invention

In light of the foregoing, the present invention enables an examiner to change the sound speed in a desired local region in a simple, intuitive and easy-to-understand manner.

DETAILED DESCRIPTION

Various embodiments of the present invention will be described below in detail with reference to the drawings.

Figure 1:
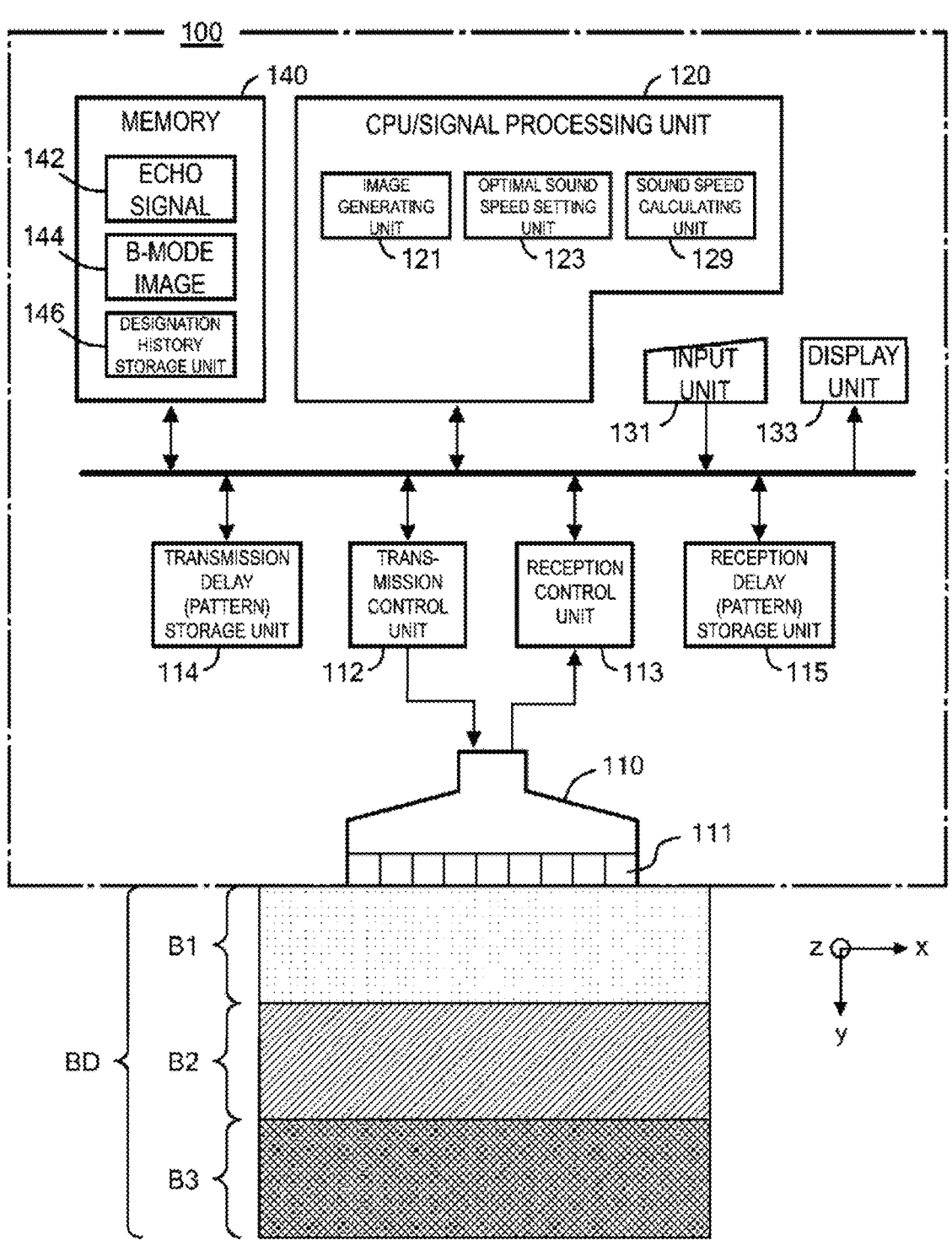
FIG. 1 is a block diagram depicting a configuration of an ultrasound diagnostic device 100 according to an embodiment.

FIG. 1 is a block diagram depicting a configuration of an ultrasound diagnostic device 100 according to a specific embodiment of the present invention. The ultrasound diagnostic device 100 includes an ultrasonic probe 110, a memory 140, and a CPU 120. The CPU 120 can function as a signal processing device. The ultrasound diagnostic device 100 includes a transmission control unit 112, a reception control unit 113, a transmission delay (pattern) storage unit 114, and a reception delay (pattern) storage unit 115. Furthermore, the ultrasound diagnostic device 100 includes an input unit 131 and a display unit 133. The input unit 131 can receive input from an operator, for example, receiving input of information such as instructions, positions, and numerical values from an operator via a graphical user interface. The input unit 131 includes a keyboard, hard keys, soft keys, and the like. The input unit 131 may include various input devices such as pointing devices like mice, touch panels, pen tablets, touch pads, track balls, and joy sticks, as well as eye tracking, voice input, and the like. The display unit 133 may include display devices such as LCDs (Liquid Crystal Display), glasses-type or goggle-type head mount displays, and projectors.

An ultrasonic probe 110 includes a plurality of elements (transducers) 111 that form a one-dimensional or two-dimensional transducer array. The plurality of elements 111 transmit ultrasonic waves into a living body based on a drive signal applied from a transmission control unit 112, and receive ultrasound echoes (echo signals) reflected within the living body, and output the received signals to a reception control unit 113. For ease of understanding by the reader, nine elements 111 are depicted in the figure in the azimuth direction (X direction in FIG. 1) for simplicity, but in reality, 16 to 4000, preferably 100 to 2500, and more preferably about 2000 elements 111 can be arranged in one ultrasonic probe 110. In addition, 1 to 1000, preferably 8 to 800, and more preferably about 500 elements 111 can be arranged in one ultrasonic probe 110 in the Z direction perpendicular to the azimuth direction (X direction in FIG. 1) and the depth direction (Y direction in FIG. 1). In other words, preferably 500×2000 elements 111 can be arranged in one ultrasonic probe 110.

Each element 111 is a transducer using a material having piezoelectric properties (piezoelectric body) such as a piezoelectric ceramic, a polymer piezoelectric element, or the like. Each element 111 generates a pulsed or continuous ultrasonic wave, and the ultrasonic waves are combined to form an ultrasonic beam. Furthermore, the plurality of elements 111 expand and contract by receiving ultrasonic echoes reflected from within the subject BD, and generate electric signals. These electric signals are output to the reception control unit 113 as ultrasonic echo reception signals.

Each element 111 contacts the surface of the subject BD. In the embodiment of FIG. 1, the subject BD includes subcutaneous fat B1, muscle B2, and liver tissue B3. However, it is not essential that the examination site includes the liver tissue B3 of the subject BD. An examination subject may be any structure of an examination region of a subject BD that is to be examined by an ultrasound diagnostic device. Furthermore, the subject BD is not limited to a human body, but may be any organism other than a human, such as livestock, pets, or laboratory animals.

The transmission delay (pattern) storage unit 114 stores a plurality of transmission delays used when forming an ultrasonic beam. The transmission control unit 112 selects one pattern from among the plurality of delays stored in the transmission delay storage unit 114 in accordance with the transmission direction set in the scanning control unit 11, and sets the delay time to be given to each of the drive signals of the plurality of elements 111 based on that delay. This allows ultrasonic beams transmitted simultaneously from a plurality of elements 111 to reach the entire imaging region of the subject.

The reception delay (pattern) storage unit 115 stores a plurality of reception delays used when performing focus processing on a plurality of reception signals output from a plurality of elements 111. The reception control unit 113 selects one delay from the plurality of reception delays stored in the reception delay storage unit 115, and adds a delay to the plurality of reception signals based on the reception delay and the sound speed inside the subject.

Thereby the reception focus process is performed. This focusing process generates an echo signal in which the ultrasonic echo focus is narrowed. Furthermore, the reception control unit 113 performs envelope detection processing on the formed echo signal. The echo signals are stored in an echo signal memory 142 within the memory 140.

Herein, the delay of the received signal is determined based on the sound speed within the subject BD. In general, the average sound speed inside the human body is set to 1530 to 1540 m/s. In reality, however, the sound speed varies depending on the tissue within the subject BD. In general, the sound speed in the subcutaneous fat B1 is set to about 1450 m/s, and in muscle B2 or liver tissue B3, the sound speed is set to about 1550 m/s. However, these values are general and may vary depending on the subject. For example, the sound speed is faster in a liver with cirrhosis, and the sound speed is slower in a liver with fatty liver tissue. In this embodiment, the reception delay storage unit 115 stores delay values, for example, from 1000 m/s to 3000 m/s, and more preferably from 1430 m/s to 1580 m/s.

The CPU 120 includes an image generating unit 121, an optimal sound speed setting unit 123, and a sound speed calculating unit 129. The image generating unit 121 generates a B-mode image, which is tomographic image information relating to tissue in the subject, based on the echo signal output from the reception control unit 113. The B-mode image is stored in a B-mode image memory 144 within the memory 140. In another embodiment, the data is stored in a storage device at a remote location connected via a network. In the example of FIG. 1, a B-mode image 144 is described as an example, but the present invention is also applicable to the reconstruction of images in other modes.

The optimal sound speed setting unit 123 automatically sets the optimal sound speed for image display of a specific part based on the delay of the received signal and the echo signal 142 or the B-mode image generated by the image generating unit 121, or based on the delay of the received signal and sound speed designation information from the input unit 131.

In a specific embodiment of the present invention, the sound speed calculating unit 129 determines the phase of the echo signal 142 and determines the difference in sound speed for each sound ray. In another embodiment, the sound speed calculating unit 129 analyzes the B-mode image 144 and identifies the type and size of tissue contained in the B-mode image 144 in order to estimate the sound speed for each sound ray.

In the present embodiment, software (program) is executed by a processor including a CPU 120 to configure a signal processing unit including an image generating unit 121, an optimal sound speed setting unit 123, and a sound speed calculating unit 129. The software is stored in the memory 140. The software may be recorded on a built-in hard disk, or on other recording media such as flash memory, DVD-ROM, and the like. It is also possible to realize some or most of the functional blocks depicted in FIG. 1 using a smartphone, or to realize the blocks using a plurality of computers located in remote locations and connected via a network.

Figure 2:
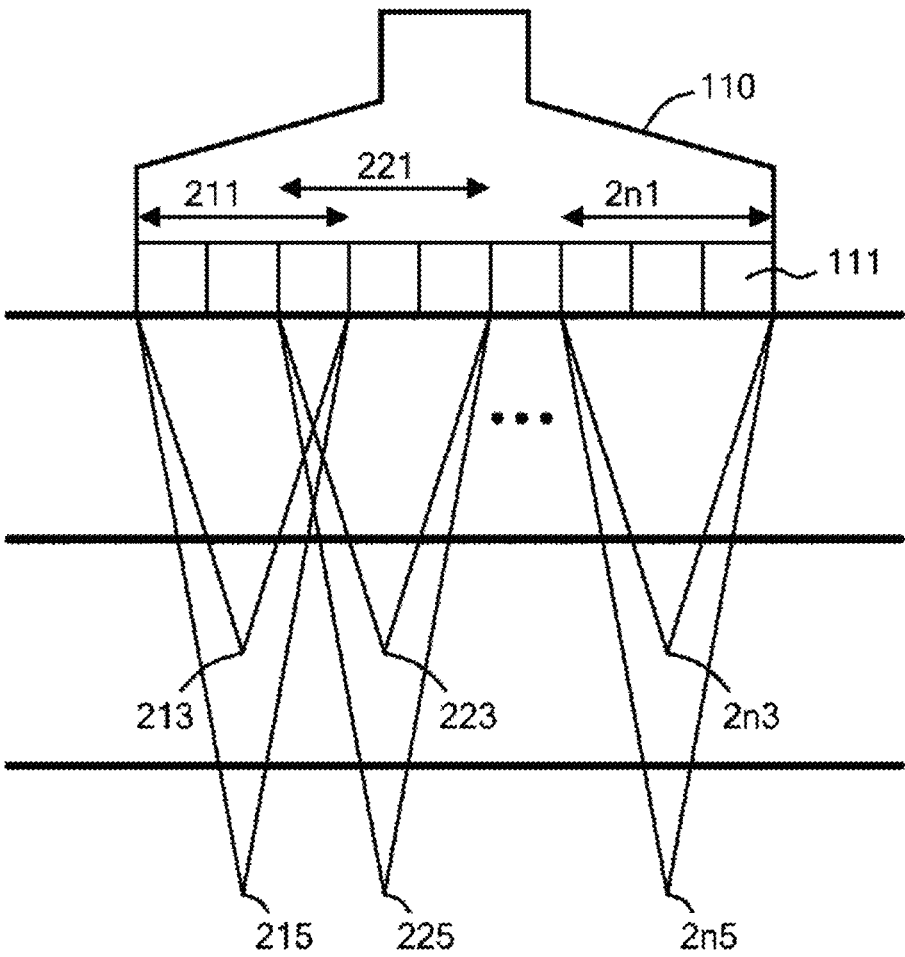
FIG. 2 is a conceptual diagram depicting a focal position inside a subject when linear scanning is performed in an azimuth direction according to an embodiment.

FIG. 2 depicts the focal position inside the subject BD when linear scanning is performed in the azimuth direction X. In this embodiment, similarly to conventional linear electronic scanning, aperture positions 211, 221 to 2n1 for transmitting and receiving waves of the element array 111 are moved in sequence, and focal positions 213, 223 to 2n3, 215, 225 to 2n5 of the transmitting and receiving waves are moved in sequence for scanning to obtain a tomographic image. According to a conventional linear electronic scanning technique, a desired number of focal points can be set at desired positions (positions in the depth direction and positions in the azimuth direction) by controlling the aperture positions and the delay at each aperture.

Figure 3:
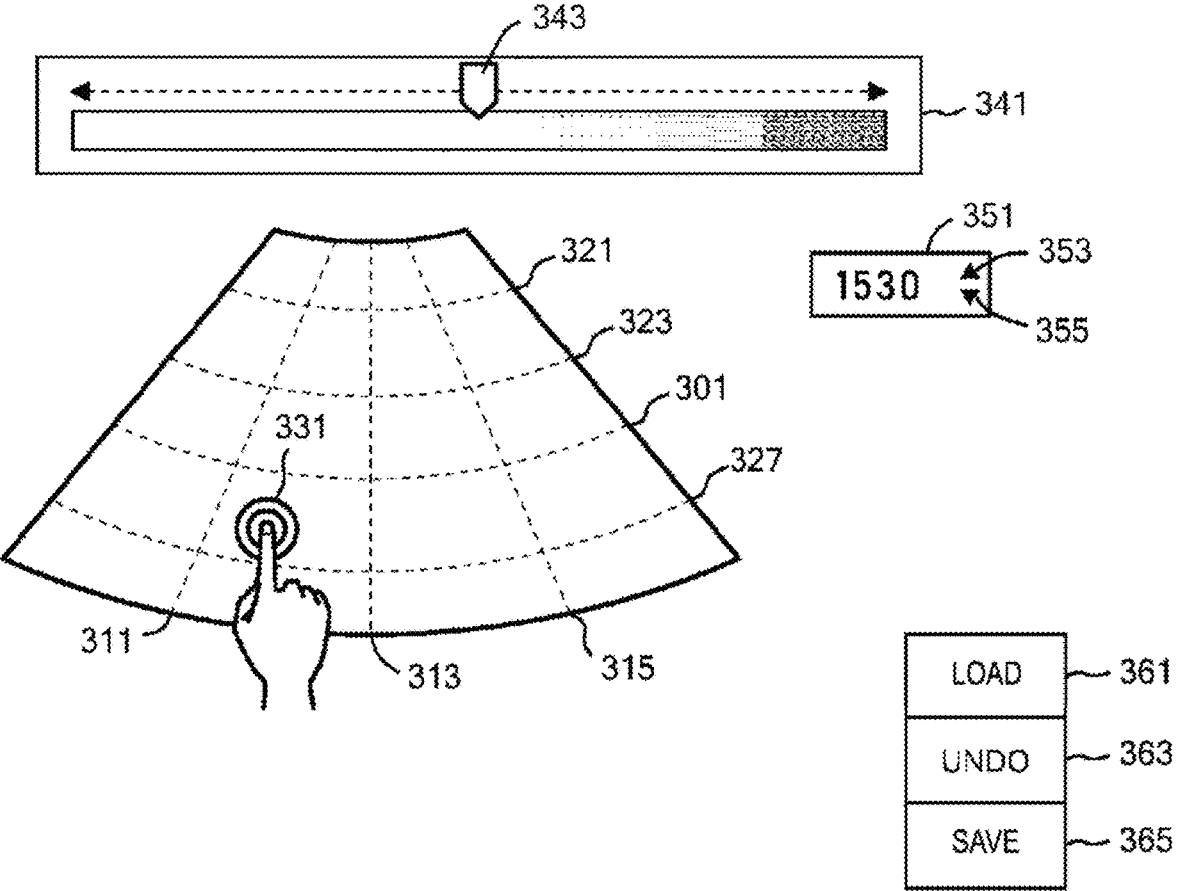
FIG. 3 is a diagram depicting a user interface that allows an operator to designate position information and a sound speed of a local region of an ultrasound image according to the embodiment.

FIG. 3 depicts an example of a user interface that allows an operator to designate position information and sound speeds of local regions of an ultrasound image in a preferred embodiment of the present invention. As depicted in the figure, the display unit 133 displays a B-mode image 301 of the subject BD currently being examined. When the operator selects an icon (not depicted) on the screen labeled "Local sound speed setting", depth direction boundary lines 311, 313, 315 and azimuth direction boundary lines 321, 323, 325, 327 are displayed superimposed on the B-mode image 301. In the example of FIG. 3, depth direction boundary lines 311, 313, and 315 extend radially in accordance with the scanning cross section of the B-mode image spreading in a fan shape. In another embodiment, the depth direction boundary lines 311, 313, 315 extend in a direction perpendicular to the azimuth direction boundary lines 321, 323, 325, 327. In the example of FIG. 3, the azimuth direction boundary lines 321, 323, 325, and 327 extend in straight lines perpendicular to the depth direction boundary line 313 located in the center. In another embodiment, the azimuth direction boundary lines 321, 323, 325, and 327 extend in curved lines constituting parts of concentric circles in accordance with the scanning cross section of the B-mode image that spreads in a fan shape.

The number, position, and shape of the depth direction boundary lines 311, 313, 315 and the azimuth direction boundary lines 321, 323, 325 can have various changes as required. In a preferred embodiment of the present invention, the number, position, and shape of the depth direction boundary lines 311, 313, 315 and the azimuth direction boundary lines 321, 323, 325 can be set on the screen by the operator. For example, the number of depth direction boundary lines 311, 313, and 315 and azimuth direction boundary lines 321, 323, and 325 may be any natural number within a range of 1 to 100. Preferably, the number of depth direction boundary lines 311, 313, and 315 and azimuth direction boundary lines 321, 323, and 325 may be any natural number within a range of 3 to 20.

Furthermore, the depth direction boundary lines 311, 313, and 315 and the azimuth direction boundary lines 321, 323, and 325 do not need to be uniform over the entire B-mode image 301, but may be dense in predetermined regions and sparse in other regions. For example, the Japan Gastroenterological Endoscopy Society has defined 25 types of recommended recording cross sections (ultrasound B-mode images), and for each cross section, the position and direction in which the operator places the ultrasonic probe 110 on the subject BD is designated. In such a case, for example, a bile duct may be of interest in the 14th cross section of the 25 cross sections, while the approximate location in the B-mode image 301 where the bile duct is located is known. In locations where the bile duct is likely to exist, one or both of the depth direction boundary lines 311, 313, 315 and the azimuth direction boundary lines 321, 323, 325 may be dense, and may be sparse in other regions. In another embodiment, organs included in the B-mode image are automatically detected, and the depth direction boundary lines 311, 313, 315 and the azimuth direction boundary lines 321, 323, 325 are positioned according to the detection results.

Figure 4:
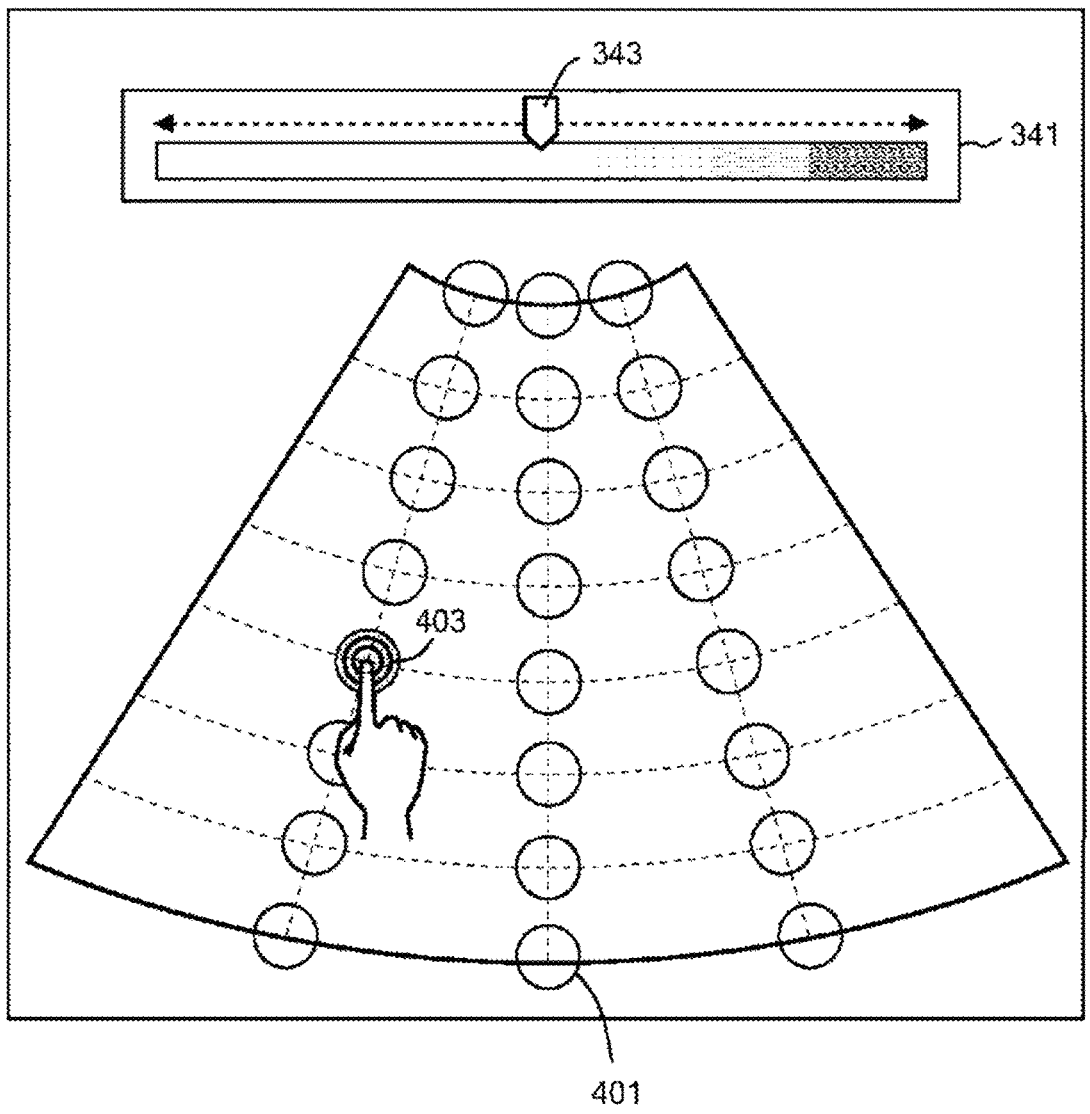
FIG. 4 is a conceptual diagram depicting a case where a plurality of position designating icons arranged in the depth direction and the azimuth direction according to an embodiment are used.

In the embodiment of FIG. 3, the regions in which the sound speeds are changed are defined by the depth direction boundary lines 311, 313, and 315 and the azimuth direction boundary lines 321, 323, 325, and 327, but various known techniques can be used to identify regions within a B-mode image. FIG. 4 depicts an embodiment in which a plurality of position designating icons 401 arranged in the depth direction Y and the azimuth direction X are used instead of the depth direction boundary lines 311, 313, 315 and the azimuth direction boundary lines 321, 323, 325, 327. The plurality of position designating icons 401 may be fixed (the position, shape, and number cannot be changed). In another embodiment, the position, shape, and number of the plurality of position designating icons 401 can be changed according to the operator's designation. In yet another embodiment, the position, shape, and number of the plurality of position designating icons 401 are automatically changed depending on the type of B-mode image. For example, the abdominal aorta may be of interest in the fourth cross section of the 25 types of recording cross sections recommended by the Japan Gastroenterological Endoscopy Society, but the approximate location of the abdominal aorta in the B-mode image 301 is known. At positions where the abdominal aorta is likely to be present, a plurality of position designating icons 401 are displayed so that the position designating icons 401 are arranged in a shape that covers the abdominal aorta. In another embodiment, organs included in the B-mode image are automatically detected, and a plurality of position designating icons 401 are arranged according to the detection results.

The position, shape and number of the plurality of position designating icons 401 can be changed using various techniques. For example, when an arbitrary position designating icon 401 is selected for a predetermined period of time, a list is displayed for selecting the individual shape of the position designating icon 401, such as circle, rectangle, fan-shape, ellipse, and the like, so that the operator can select from the list. In addition, by pinching in on two position designating icons 401 that are spaced apart in the azimuth direction, the number of position designating icons 401 in the azimuth direction can be increased, and by pinching out on two position designating icons 401 that are spaced apart in the azimuth direction, the number of position designating icons 401 in the azimuth direction can be decreased. By pinching in on two position designating icons 401 that are separated in the depth direction, the number of position designating icons 401 in the depth direction can be increased, and by pinching out on two position designating icons 401 that are separated in the depth direction, the number of position designating icons 401 in the depth direction can be decreased. By pinching in on two position designating icons 401 that are separated in both the azimuth direction and the depth direction, the number of position designating icons 401 in the azimuth direction and the depth direction can be increased simultaneously, and by pinching out on two position designating icons 401 that are separated in both the azimuth direction and the depth direction, the number of position designating icons 401 in the azimuth direction and the depth direction can be decreased simultaneously. Furthermore, pinching in on each of the position designating icons 401 can make the position designating icons 401 smaller, and pinching out on each of the position designating icons 401 can make the position designating icons 401 larger.

In FIG. 3, when a region for which a change in sound speed is desired is selected, a selection display icon 331 is displayed above the selected region. The region is selected using the input unit 131. Selection by the input unit 131 includes selection by pointing devices such as a mouse, a touch panel, a pen tablet, a touch pad, a trackball, and a joystick, as well as selection by keyboard input. When the input by the input unit 131 is a keyboard input, the region is selected by moving through the regions in order using the tab key or by keying in the number assigned to each region. Moreover, instead of or in addition to a pointing device or keyboard input, the region can be selected by various input devices such as eye tracking or voice input. In this embodiment, the selection display icon 331 displays a plurality of concentric circles spreading at a predetermined speed only within the selection region, like ripples spreading across the surface of a pond when a pebble is thrown in, clearly indicating to the operator the range (boundary) of the selection region. In another embodiment, the selected region may be altered using a predetermined color, shading, contrast change, blinking, or the like to clearly indicate to the operator the range (boundary) of the selected region. In yet another embodiment, the perimeter of the selected region is displayed differently using a predetermined color, shading, blinking, or the like, to clearly show the range (boundary) of the selected region to the operator. In yet another embodiment, the display of the selected region is not changed, and the display of regions other than the selected region is changed using a predetermined color, shading, change in contrast, blinking, or the like, to clearly indicate the extent (boundary) of the selected region to the operator. In other words, in response to one or more of the plurality of image items being selected, the manner in which the selected one or more plurality of image items are displayed is changed so that those image items can be distinguished from the other one or more plurality of image items that were not selected. The region surrounded by the depth direction boundary lines 311, 313, and 315 and the azimuth direction boundary lines 321, 323, 325, and 327 corresponds to the "image item" referred to herein. The selected region is localized or limited in both the azimuth direction and the depth direction. The size and/or number of the plurality of image items can be changed automatically or manually.

In FIG. 4, when selecting a position designating icon 401 corresponding to a region in which a change in the sound speed is desired, the selected position designating icon 401 changes to a selection display icon 403. The selection display icon 403 can be distinguished from the position designating icon 401 in terms of color, shape, pattern, blinking, or the like. In other words, in response to one or more of the plurality of image items being selected, the manner in which the selected one or more plurality of image items are displayed is changed so that those image items can be distinguished from the other one or more plurality of image items that were not selected. The position designating icon 401 corresponds to the "image item" referred to herein. The position designating icon 401 is localized or limited in both the azimuth direction and the depth direction. The image generating unit 121 displays a plurality of image items that are candidates for local regions superimposed on the B-mode image 144. The plurality of image items are arranged in an azimuth direction and a depth direction, and position information of a local region is designated in response to selecting one or more of the plurality of image items.

The position designating icon 401 is selected by the input unit 131. Selection by the input unit 131 includes selection by pointing devices such as a mouse, a touch panel, a pen tablet, a touch pad, a trackball, and a joystick, as well as selection by keyboard input. If the input via the input unit 131 is a keyboard input, the region is selected by moving the selected position designating icon 401 in order using a tab key or by keying in numbers assigned to the position designating icons 401. Moreover, instead of or in addition to a pointing device or keyboard input, the position designating icon 401 can be selected by various input devices such as eye tracking or voice input. In one embodiment, the selected region is only the region within the selection display icon 403. In another embodiment, the selected region includes not only the region within the selection display icon 403 but also the outside region thereof.

In FIG. 3, when selecting a region in which a change in the sound speed is desired, a slider icon 341 is displayed on the display unit 133 together with the B-mode image 301. The slider icon 341 has a slide handle 343. When the operator moves the slide handle 343 to the right, the sound speed becomes faster, and when the operator moves the slide handle 343 to the left, the sound speed becomes slower. In a preferred embodiment of the present invention, the speed is adjustable according to a predetermined linear function between 1000 m/s and 2000 m/s with 1500 m/s as the center. In another embodiment of the present invention, the speed is adjustable according to a predetermined nonlinear function between 1200 m/s and 3000 m/s with 1530 m/s as the center. In this example, near the center, the distance traveled from the center and the change in sound speed are proportional to each other, but a function is selected that includes a curve in which the change in sound speed with respect to the distance traveled is very large near the right end, for example. In a particular embodiment of the present invention, in response to the operator moving the slide handle 343 to the right, the signal processing unit 120 generates a high-pitched sound from a speaker (not depicted) corresponding to a faster sound speed, and in response to the operator moving the slide handle 343 to the left, the signal processing unit 120 generates a low-pitched sound from the speaker corresponding to a slower sound speed.

In a particular embodiment of the present invention, in addition to the slider icon 341 or instead of the slider icon 341, a dialog box such as a spin box 351 or a dial icon corresponding to each of the levels from 1000 is also displayed on the display unit 133. The value displayed in the spin box 351 is linked to the position of the slide handle 343 in the slider icon 341, and when the slide handle 343 is moved, the sound speed corresponding to the moved position is displayed in the spin box 351. The value in the spin box 351 can be changed by operating up/down buttons 353, 355 on the right edge of the spin box 351, and the position of the slide handle 343 of the slider icon 341 automatically moves accordingly. The value in the spin box 351 can also be changed by inputting a value via the input unit 131 (for example, keyboard input or voice input).

In a particular embodiment of the present invention, a load button 361, an undo button 363 and a save button 365 are displayed on the display 133. As described with respect to FIG. 3, when selecting a region for changing the sound speed, a selection display icon 331 is displayed above the selected region. When the load button 361 is selected in this state, the information stored in the designation history storage unit 146 is presented in a selectable manner. The designation history storage unit 146 stores sound speeds previously set for each region. Specifically, previously set sound speeds are listed from 1 to 100 for each region. More preferably, previously set sound speeds are listed from 2 to 10 for each region. In a specific embodiment of the present invention, each region has a different upper limit on the number of sound speeds that can be stored. In a specific embodiment of the present invention, when the load button 361 is pressed once, the most recently set sound speed is recalled and displayed in the spin box 351, and the slider icon 341 is also moved to this value. When the load button 361 is pressed, for example, three times, the sound speed that was set three times previously is called up and displayed in the spin box 351, and the slider icon 341 is also moved to this value. In a specific embodiment of the present invention, when the load button 361 is pressed one or more times, previously set sound speeds are recalled and displayed as a list. When the operator selects a desired value from the list, the selected value is displayed in the spin box 351, and the slider icon 341 also moves to this value. The sound speeds displayed in the list can be modified or deleted. In a specific embodiment of the present invention, when the load button 361 is selected and a region for changing the sound speed is not selected, a display and/or audio is provided to prompt the operator to select the region for which the sound speed is to be changed.

In a specific embodiment of the present invention, when selecting a region in which the sound speed is to be changed, the sound speed to be applied to the selected region is set, and then the save button 365 is selected, position information of the local region of the ultrasound image and the sound speed set corresponding thereto are sent to the image generating unit 121. The region for which the sound speed is to be changed does not have to be a single region, and any plurality of consecutive regions or plurality of regions separated from each other can be selected and a common sound speed can be set for these plurality of regions. The image generating unit 121 receives the position information of a local region of the ultrasound image and the sound speed set corresponding thereto, and reconstructs the image according to the position information of the local region of the ultrasound image and the sound speed that was set corresponding thereto. More specifically, the image generating unit 121 identifies all focus points corresponding to position information of a local region of the ultrasound image, and uses the sound speed set for reception beamforming at all identified focus points. When executing a phase align and sum process in which echo signals received by each of the ultrasonic transducers are delayed and summed, a delay corresponding to a set sound speed is applied. In a specific embodiment of the present invention, the delay pattern stored in the reception delay storage unit 115 is updated to the position information of the local region of the ultrasound image received by the image generating unit 121 and the sound speed set corresponding to the position information. In a specific embodiment of the present invention, the delay pattern stored in the transmission delay storage unit 114 is updated to the position information of the local region of the ultrasound image received by the image generating unit 121 and the sound speed set corresponding to the position information. In a specific embodiment of the present invention, the sound speeds previously set for each region stored in the designation history storage unit 146 are updated according to the position information of the local region of the ultrasound image received by the image generating unit 121 and the sound speed set corresponding to the position information. In the local region designated by the operator, the delay is changed according to the designated sound speed as described above, but the sound speed in regions other than the local region remains unchanged. This allows the sound speed in the local region to be changed so as to be different from the sound speed in regions other than the local region. The local region is local in both the azimuth direction and the depth direction.

In a specific embodiment of the present invention, a B-mode image 144 is generated covering the entire region using sound speeds of the local region and sound speeds of regions other than the local region, and these regions are then cut and pasted together. This cutting and pasting may be performed on two B-mode images 144, but if a plurality of combinations of local regions and corresponding sound speeds are set, cutting and pasting is performed on three or more B-mode images 144. The B-mode image 144 to be cut and pasted does not need to be a B-mode image 144 covering the entire region, but may be localized in the azimuth direction, depth direction, or both, so long as the required region is covered.

In a specific embodiment of the present invention, a sound speed once defined by selecting the SAVE button 365 can be canceled by pressing the UNDO button 363. The most recent sound speed (the sound speed immediately prior to selecting the save button 365) stored in the designation history storage unit 146 and the position information of the local region are sent to the image generating unit 121. The image generating unit 121 receives the position information of a local region of the ultrasound image and the sound speed set corresponding thereto, and reconstructs the image according to the position information of the local region of the ultrasound image and the sound speed that was set corresponding thereto. More specifically, the image generating unit 121 identifies all focus points corresponding to position information of a local region of the ultrasound image, and uses the sound speed set for reception beamforming at all identified focus points. When executing a phase align and sum process in which echo signals received by each of the ultrasonic transducers are delayed and summed, a delay corresponding to a set sound speed is applied. In a specific embodiment of the present invention, the delay pattern stored in the reception delay storage unit 115 is updated to the position information of the local region of the ultrasound image received by the image generating unit 121 and the sound speed set corresponding to the position information. In a specific embodiment of the present invention, the delay pattern stored in the transmission delay storage unit 114 is updated to the position information of the local region of the ultrasound image received by the image generating unit 121 and the sound speed set corresponding to the position information. In a specific embodiment of the present invention, the image generating unit 121 updates the sound speed previously set in each region stored in the designation history storage unit 146 so that the sound speed at the time that the save button 365 was pressed is deleted for the local region. In a specific embodiment of the present invention, pressing the UNDO button 363 a plurality of times not only returns the sound speed information setting to the previous state, but can also return the sound speed information setting to two or more previous states.

Returning to FIG. 2 to continue the description, a human body as the subject typically has tissues with different sound speeds, such as skin, fat, muscle, and organ parenchyma, arranged in layers as depicted in regions B1, B2, and B3 in FIG. 2, in order from the body surface side close to the element array 111 of the probe. Delay time correction values at the shallow focus position 213 and the deep focus position 215 at the aperture position 211 are significantly different, but the distribution of delay time correction values corresponding to the focal points 223 and 225 with the same focal length as nearby aperture position 221 is generally very close to the correction values corresponding to the focal lengths 213 and 215, respectively. Based on this characteristic, the distribution of optimal delay time correction values for each focal length at the initial aperture position 211 can be used as the initial value for the procedure of optimizing the delay time correction values at an adjacent aperture position 221.

However, even if the echo signals are from foci having the same focal distance at aperture positions that are close to each other, the sound speeds of the ultrasonic waves in the biological tissue through which the waves propagate may differ. If the sound speed set for determining the delay time differs from the actual sound speed, the reception focus will be degraded, the spatial resolution deteriorates, and a preferable contrast cannot be obtained.

When there is a difference in the sound speed of the ultrasonic waves propagating through the biological tissue between two echo signals from foci with the same focal distance at adjacent aperture positions, the phases of the two echo signals will be different. By automatically changing the sound speed (delay time correction value) according to the degree of phase difference of the echo signals, the spatial resolution can be improved, and a preferable contrast can be obtained. In one embodiment of the present invention, the phases of n echo signals from focal points with the same focal distance are analyzed, and the sound speeds (delay time correction values) of the echo signals that deviate from the average value by a predetermined standard deviation are modified. In such a case, n may preferably be a predetermined natural number within the range of 3 to 1000. More preferably, n may be a predetermined natural number within the range of 10 to 500. In another embodiment of the present invention, the value of n can be manually changed by an operator. Furthermore, echo signals whose phase difference is outside a predetermined deviation range of $0.1\sigma$ to $\pm 4\sigma$ can be subject to an automatic change in sound speed. Preferably, echo signals whose phase difference is outside a predetermined deviation range of $0.5\sigma$ to $\pm 2\sigma$ can be subject to an automatic change in sound speed. More preferably, echo signals whose phase difference is outside the range of $1\sigma$ can be subject to an automatic change in sound speed. In another embodiment of the present invention, the value of the predetermined deviation range can be manually changed by an operator.

In another embodiment of the present invention, the invention described in Japanese Patent No. 6081744 is utilized in setting the sound speed for each focal point. The echo signals are reconstructed to generate a B-mode image, the thickness of the subcutaneous fat (and optionally muscle thickness) contained in the B-mode image is measured, and the optimal sound speed for each focus is set according to the measured fat thickness (and optionally muscle thickness). In another embodiment of the present invention, the difference in the phase of the echo signals is determined by taking into account the difference in measured fat thickness (and optionally muscle thickness). The sound speed (delay time correction value) is automatically changed in accordance with the phase difference of the determined echo signals.

In the present embodiment, software (program) is executed by a processor including a CPU 120 to configure an image generating unit 121, an optimal sound speed setting unit 123, and a sound speed calculating unit 129. The software is stored in the memory 140. The software may be recorded on a built-in hard disk, or on other recording media such as flash memory, DVD-ROM, and the like.

The present invention has been described above with a focus on the most preferred embodiment. However, as will be apparent to those skilled in the art, the present invention can be implemented by making various changes and modifications to the embodiments within the technical scope of the present invention.

REFERENCE NUMERALS

100. Ultrasound diagnostic device
110. Ultrasonic probe
111. Transducer
112. Communication control unit
113. Reception control unit
114. Transmission delay (pattern) storage unit
115. Reception delay (pattern) storage unit
120. CPU/signal processing means/signal processing unit
121. Image generating unit
123. Optimum sound speed setting unit
129. Sound speed calculating unit
131. Input unit
133. Display unit
140. Memory
142. Echo signal
144, 301. B-mode image
146. Designation history storage unit
211, 221 to 2n1. Aperture position
213, 223 to 2n3, 215, 225 to 2n5. Focus position
311, 313, 315. Depth direction boundary line
321, 323, 325, 327. Azimuth direction boundary line
331, 403. Selection display icon
341. Slider icon
343. Slide handle
351. Spin box
353. Up button
355. Down button
361. Load button
363. UNDO button
365. Save button
401. Position designating icon

The invention claimed is:

1. An ultrasound diagnostic device that generates an ultrasound image based on an echo signal from a subject, comprising:

a probe configured to perform an ultrasound scan on a tissue to be imaged, the probe comprising:

a transducer configured to transmit an ultrasound signal and receive an echo signal;

a matching layer configured to have an acoustic impedance between a tissue to be imaged and a material of the transducer; and a damping block configured to absorb ultrasound energy;

an interface configured to obtain an operator input designating position information of a local region of an ultrasound image; and at least one processor configured to change a sound speed in the local region based on the position information so as to be different from a sound speed in a region other than the local region when reconstructing the echo signal to reconstruct an ultrasound image;

wherein the local region is local in both the azimuth direction and the depth direction, wherein the at least one processor is configured to mutually associate and store information related to: past position designation history of position information of the local region; and past manual sound speed designation history of sound speed information of the local region;

wherein the at least one processor is further configured to execute one or more of the following:

returning settings of the sound speed information to one or more previous states for one or more local regions included in the past position designation history;

saving the settings of the sound speed information for the one or more local regions included in the past position designation history; and loading previously set sound speed information for the one or more local regions included in the past position designation history.

2. The ultrasound diagnostic device according to claim 1, wherein the change in the sound speed is performed according to a manual instruction by an operator, and the manual instruction is performed in accordance with one or more of:

a slide operation by an operator of a slide bar displayed on a display device of the ultrasound diagnostic device; and input of a numerical value into a dialogue box displayed on a display device of the ultrasound diagnostic device by an operator.

3. The ultrasound diagnostic device according to claim 1, wherein the change in the sound speed is performed by analyzing the echo signal and/or the ultrasound image corresponding to the local region.

4. The ultrasound diagnostic device according to claim 3, wherein the at least one processor is further configured to calculate the sound speed of the local region based on a phase difference between the echo signal and another echo signal.

5. The ultrasound diagnostic device according to claim 1, wherein the at least one processor is further configured to control a display to display a plurality of image items that are candidates for the local region by superimposing on the ultrasound image; wherein the plurality of image items are arranged in the azimuth direction and the depth direction; and the position information of the local region is designated in response to selection of one or more of the plurality of image items.

6. The ultrasound diagnostic device according to claim 5, wherein the size and/or number of the plurality of image items can be changed automatically or manually.

7. The ultrasound diagnostic device according to claim 5, wherein the at least one processor is configured to change a display manner in response to one or more of the plurality of image items being selected, so that the selected one or more of the plurality of image items are distinguishable from one or more of the plurality of image items that were not selected.

8. The ultrasound diagnostic device according to claim 1, wherein the processor is further configured to:

generate the ultrasound image of the local region by reconstructing the echo signals using delay or sound speed parameters corresponding to the sound speed of the local region; and generate an ultrasound image of a region other than the local region by reconstructing the echo signals using delay or sound speed parameters corresponding to the sound speed of the region other than the local region.

9. A method for generating an ultrasound image based on an echo signal from a subject, the method comprising:

receiving the echo signal;

receiving position information of a local region of an ultrasound image based on a designation by an operator;

changing a sound speed in the local region based on the position information so as to be different from a sound speed in a region other than the local region when reconstructing the echo signal to reconstruct the ultrasound image;

mutually associating and storing past position designation history of position information of the local region and past manual sound speed designation history of sound speed information of the local region; and returning settings of the sound speed information to one or more previous states for one or more local regions included in the past position designation history, saving the settings of the sound speed information for the one or more local regions included in the past position designation history, or loading previously set sound speed information for the one or more local regions included in the past position designation history, wherein the local region is localized in both the azimuth direction and the depth direction.

10. A non-transitory storage medium storing instructions that when executed by a processor cause the processor to:

receive an echo signal;

receive position information of a local region of an ultrasound image based on a designation by an operator;

change a sound speed in the local region based on the position information so as to be different from a sound speed in a region other than the local region when reconstructing the echo signal to reconstruct an ultrasound image;

mutually associate and store past position designation history of position information of the local region and past manual sound speed designation history of sound speed information of the local region; and return settings of the sound speed information to one or more previous states for one or more local regions included in the past position designation history, save the settings of the sound speed information for the one or more local regions included in the past position designation history, or load previously set sound speed information for the one or more local regions included in the past position designation history, wherein the local region is localized in both the azimuth direction and the depth direction.

11. The ultrasound diagnostic device according to claim 1, wherein the local region has an upper limit on a number of sound speeds that can be stored as compared to the region other than the local region.

12. The ultrasound diagnostic device according to claim 1, wherein the at least one processor is configured to:

detect organs in the ultrasound image; and display depth direction boundary lines and azimuth direction boundary lines on the ultrasound image at positions based on detecting the organs.

13. The ultrasound diagnostic device according to claim 1, wherein the at least one processor is configured to:

detect organs in the ultrasound image; and display designating icons on the ultrasound image in an arrangement based on detecting the organs.

14. The ultrasound diagnostic device according to claim 1, wherein the at least one processor is configured to:

display first depth direction boundary lines and first azimuth direction boundary lines on the ultrasound image with a first density in a first region of the ultrasound image; and display second depth direction boundary lines and second azimuth direction boundary lines on the ultrasound image with a second density, that is different than the first density, in a second region of the ultrasound image.

15. The ultrasound diagnostic device according to claim 1, wherein the at least one processor is configured to:

set a common sound speed for a plurality of consecutive regions.

16. The ultrasound diagnostic device according to claim 1, wherein the at least one processor is configured to:

set a common sound speed for a plurality of separated regions.

17. The method of claim 9, wherein the local region has an upper limit on a number of sound speeds that can be stored as compared to the region other than the local region.

18. The method of claim 9, further comprising:

displaying first depth direction boundary lines and first azimuth direction boundary lines on the ultrasound image with a first density in a first region of the ultrasound image; and displaying second depth direction boundary lines and second azimuth direction boundary lines on the ultrasound image with a second density, that is different than the first density, in a second region of the ultrasound image.

19. The non-transitory storage medium of claim 10, wherein the local region has an upper limit on a number of sound speeds that can be stored as compared to the region other than the local region.

20. The non-transitory storage medium of claim 10, wherein the instructions further cause the processor to:

display first depth direction boundary lines and first azimuth direction boundary lines on the ultrasound image with a first density in a first region of the ultrasound image; and display second depth direction boundary lines and second azimuth direction boundary lines on the ultrasound image with a second density, that is different than the first density, in a second region of the ultrasound image.

* * * * *